US00PP27495P2

(12) United States Plant Patent
Kretz

(10) Patent No.: US PP27,495 P2
(45) Date of Patent: Dec. 20, 2016

(54) ***LYCHNIS* PLANT NAMED 'LYCHJENPET'**

(50) Latin Name: *Lychnis flos-cuculi*
Varietal Denomination: Lychjenpet

(71) Applicant: Jennifer Anne Kretz, Blanford Forum (GB)

(72) Inventor: Jennifer Anne Kretz, Blanford Forum (GB)

( * ) Notice: Subject to any disclaimer, the term of this patent is extended or adjusted under 35 U.S.C. 154(b) by 0 days.

(21) Appl. No.: 14/545,814

(22) Filed: Jun. 23, 2015

(51) Int. Cl.
*A01H 5/02* (2006.01)

(52) U.S. Cl.
USPC ..... Plt./452

(58) Field of Classification Search
USPC ..... Plt./452
See application file for complete search history.

(56) References Cited

PUBLICATIONS

PLUTO Plant Variety Database Jul. 19, 2016. p. 1.*

* cited by examiner

*Primary Examiner* — Annette Para
(74) *Attorney, Agent, or Firm* — C. A. Whealy

(57) ABSTRACT

A new and distinct cultivar of *Lychnis* plant named 'Lychjenpet', characterized by its compact, upright and uniformly mounded plant habit; freely basal clumping growth habit, dense and bushy plants; moderately vigorous growth habit; freely flowering habit; bright pink-colored double flowers arranged on short dense spikes; and good garden performance.

2 Drawing Sheets

Botanical designation: *Lychnis flos-cuculi.*
Cultivar denomination: 'LYCHJENPET'.

BACKGROUND OF THE INVENTION

The present invention relates to a new and distinct *Lychnis* plant, botanically known as *Lychnis flos-cuculi*, commonly referred to as Ragged Robin, and hereinafter referred to by the name 'Lychjenpet'.

The new *Lychnis* plant is a naturally-occurring whole plant mutation of *Lychnis flos-cuculi* 'Lychjen', disclosed in U.S. Plant Pat. No. 14,139. The new *Lychnis* plant was discovered and selected by the Inventor as a single flowering plant within a population of plants of 'Lychjen' in May, 2004 in a controlled greenhouse environment in Bressingham Diss, Norfolk, United Kingdom.

Asexual reproduction of the new *Lychnis* plant by basal cuttings in a controlled greenhouse environment in Bressingham Diss, Norfolk, United Kingdom since July, 2004 has shown that the unique features of this new *Lychnis* plant are stable and reproduced true to type in successive generations.

SUMMARY OF THE INVENTION

The new *Lychnis* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lychjenpet'. These characteristics in combination distinguish 'Lychjenpet' as a new and distinct *Lychnis* plant:

1. Compact, upright and uniformly mounded plant habit.
2. Freely basal clumping growth habit, dense and bushy plants.
3. Moderately vigorous growth habit.
4. Freely flowering habit.
5. Bright pink-colored double flowers arranged on short dense spikes.
6. Good garden performance.

Plants of the new *Lychnis* differ primarily from plants of the parent, 'Lychjen', in plant height and flowering stem length as plants of the new *Lychnis* are about half as tall as plants of 'Lychjen' and have much shorter flowering stems than plants of 'Lychjen'. In addition, plants of the new *Lychnis* have smaller leaves than plants of 'Lychjen'.

Plants of the new *Lychnis* can be compared to plants of unnamed selections of *Lychnis flos-cuculi* known to the Inventor, not patented. In side-by-side comparisons conducted in Bressingham Diss, Norfolk, United Kingdom, plants of the new *Lychnis* are about half as tall as the unnamed selections of *Lychnis flos-cuculi* known to the Inventor. In addition, plants of the new *Lychnis* have double flowers whereas plants of unnamed selections of *Lychnis flos-cuculi* known to the Inventor have single-type flowers.

BRIEF DESCRIPTION OF THE PHOTOGRAPHS

The accompanying colored photographs illustrate the overall appearance of the new *Lychnis* plant showing the colors as true as it is reasonably possible to obtain in colored reproductions of this type. Colors in the photographs may differ slightly from the color values cited in the detailed botanical description which accurately describe the colors of the new *Lychnis* plant.

The photograph on the first sheet is a side perspective view of typical plants of 'Lychjenpet' grown in an outdoor nursery.

The photograph on the second sheet is a close-up view of a typical flowering plant of 'Lychjenpet'.

DETAILED BOTANICAL DESCRIPTION

The aforementioned photograph and following observations, measurements and values describe plants grown during the summer in 5-liter containers and in ground beds in an outdoor nursery in Bressingham Diss, Norfolk, United Kingdom and under cultural practices typical of commercial *Lychnis* production. During the production of the plants, day temperatures ranged from 18° C. to 22° C. and night temperatures ranged from 6° C. to 15° C. Plants were two years old when the photographs and the description were taken. In the following description, color references are made to The Royal Horticultural Society Colour Chart, 2000 Edition, except where general terms of ordinary dictionary significance are used.

Botanical classification: *Lychnis flos-cuculi* 'Lychjenpet'.

Parentage: Naturally-occurring whole plant mutation of *Lychnis flos-cuculi* 'Lychjen', disclosed in U.S. Plant Pat. No. 14,139.

Propagation:

*Type*.—By basal cuttings.

*Time to initiate roots, summer*.—About 15 days at temperatures about 20° C.

*Time to produce a rooted young plant, summer*.—About ten days at temperatures about 15° C. to 20° C.

*Root description*.—Fine, fibrous; close to 156D in color.

*Rooting habit*.—Freely branching; dense.

Plant description:

*Plant and growth habit*.—Herbaceous perennial; basally clumping plant habit with leaves developing from the base; relatively compact, upright and uniformly mounded plant habit; moderately vigorous growth habit.

*Plant height, soil level to top of inflorescences*.—About 35 cm to 45 cm.

*Plant diameter or spread*.—About 35 cm.

Leaf description:

*Arrangement*.—Leaves arranged in basal clumps; leaves simple and sessile.

*Length*.—About 8 cm to 10 cm.

*Width*.—About 2 cm.

*Shape*.—Oblanceolate.

*Apex*.—Acute.

*Base*.—Cuneate.

*Margin*.—Entire.

*Texture, upper surface*.—Slightly pubescent, rough.

*Texture, lower surface*.—Glabrous, rough.

*Venation pattern*.—Reticulate.

*Color*.—Developing leaves, upper surface: Close to 138A flushed with close to 182A. Developing leaves, lower surface: Close to 138B. Fully expanded leaves, upper surface: Close to 138B; venation, close to 138C. Fully expanded leaves, lower surface: Close to 138B; venation, close to 139C.

Flower description:

*Flower type and flowering habit*.—Double flowers with reproductive organs transformed into petal-like structures; flowers arranged in compound dichasial cymes on relatively short flowering stems; flowering stems arising from basal clumps, mostly erect to outwardly spreading; flowers face mostly upright to outwardly; each cyme with about 30 flowers and about 450 to 500 flowers developing per plant over the flowering season; flowers face mostly outward to slightly upright.

*Fragrance*.—None detected.

*Time of flowering*.—In the United Kingdom, plants flower continuously from May to the end of June; flowering intermittent during the summer.

*Flower longevity*.—Individual flowers last about four weeks on the plant; flowers persistent.

*Inflorescence length*.—About 35 cm to 45 cm.

*Inflorescence width*.—About 12 cm.

*Flower diameter*.—About 3 cm by 3.5 cm.

*Flower depth (height)*.—About 1.5 cm.

*Flower buds*.—Height: About 5 mm. Diameter: About 5 mm. Shape: Rounded. Color: Close to 73B.

*Petals*.—Quantity and arrangement: About 35 petals in a rosette. Length: About 2 cm. Width: About 4 cm. Shape: Flabellate. Apex: Emarginate. Base: Acuminate. Margin: Entire. Texture, upper and lower surfaces: Smooth, glabrous; satiny. Color: When opening, upper surface: Close to 73A. When opening, lower surface: Close to 73B. Fully opened, upper surface: Close to 63D and 62A; color becoming closer to 62A to 62B with development. Fully opened, lower surface: Close to 62A; color becoming closer to 62B with development.

*Sepals*.—Quantity and arrangement: Six sepals in a single whorl. Length: About 2 mm. Width: About 2 mm. Shape: Oblong. Apex: Acute. Base: Cuneate. Margin: Entire. Texture, upper and lower surfaces: Smooth, glabrous. Color: When opening and fully opened, upper surface: Close to 70A. When opening and fully opened, lower surface: Close to 70B.

*Peduncles*.—Length: About 2 cm to 3 cm. Diameter: About 1.5 mm to 2 mm. Strength: Strong. Aspect: About 45° from vertical. Texture: Smooth, glabrous. Color: Close to 138A flushed with close to 182A.

*Reproductive organs*.—None observed, all transformed into petal-like structures.

*Seeds*.—Seed production has not been observed on plants of the new *Lychnis*; flowers are sterile.

Disease & pest resistance: Resistance to pathogens and pests common to *Lychnis* plants has not been observed on plants of the new *Lychnis* grown under commercial production conditions.

Garden performance: Plants of the new *Lychnis* have been observed to have good garden performance to have good tolerance to rain, wind and temperatures ranging from −20° C. to 30° C.

It is claimed:

1. A new and distinct *Lychnis* plant named 'Lychjenpet' as illustrated and described.

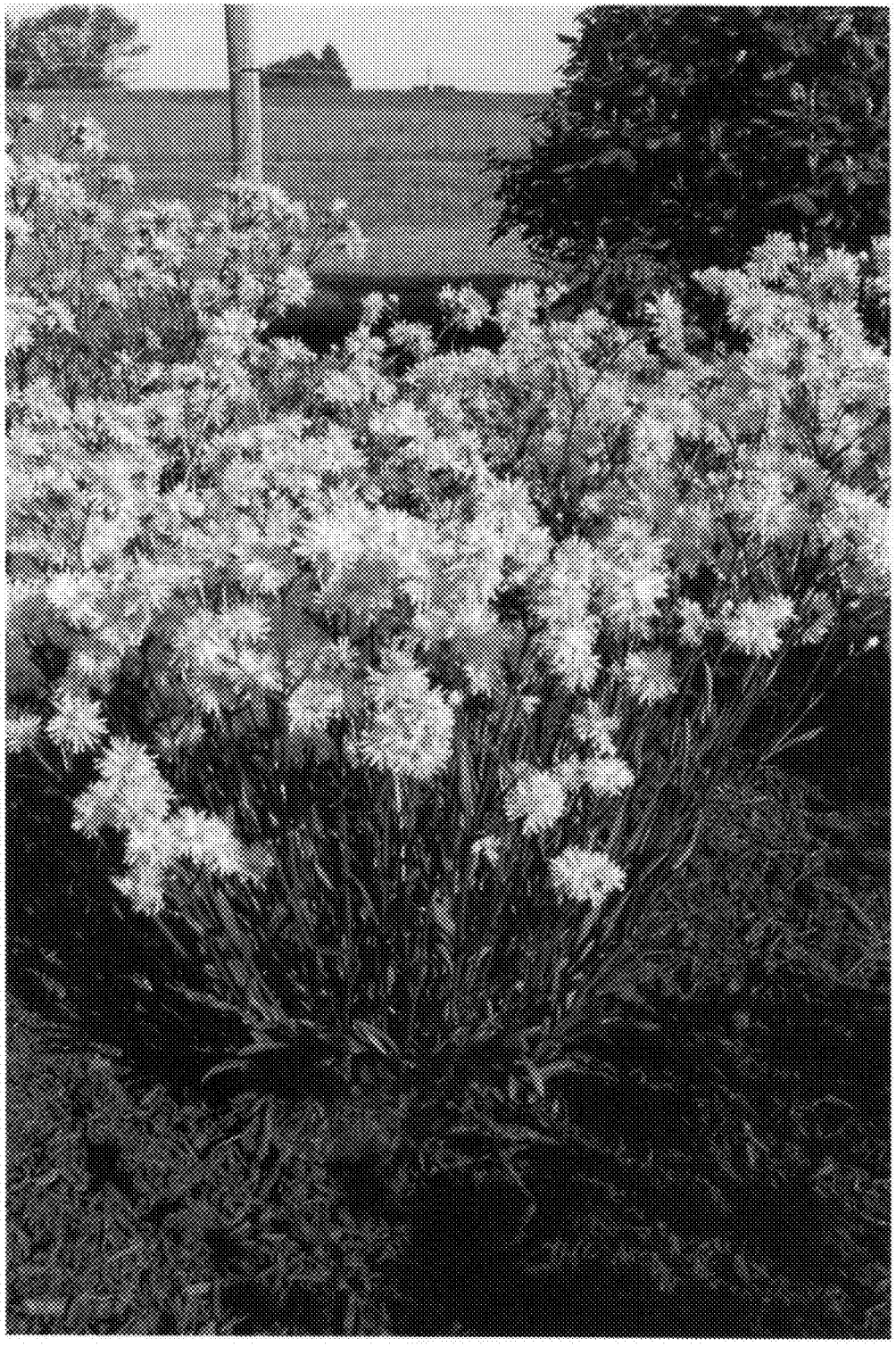

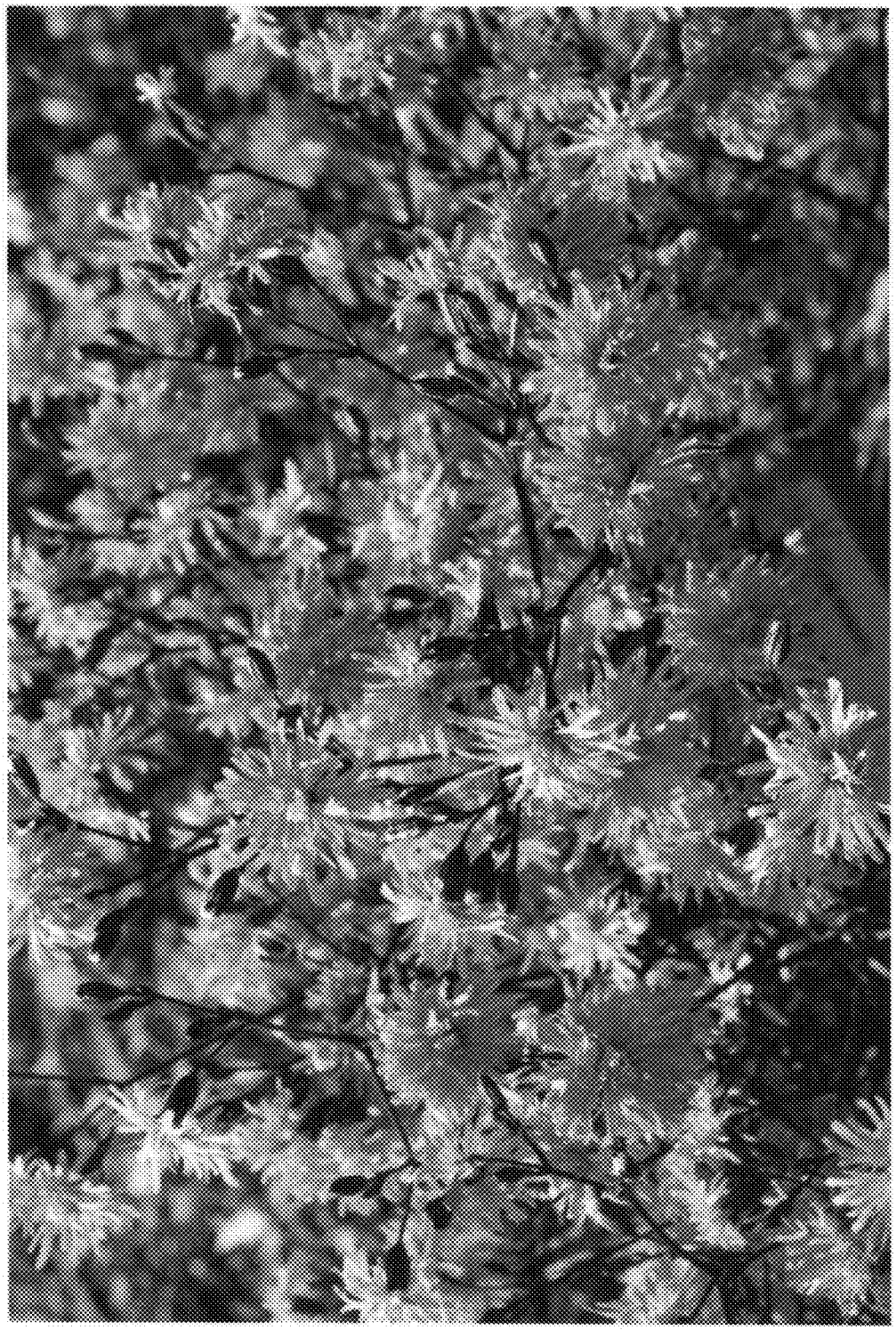

* * * * *